United States Patent [19]

Smith

[11] Patent Number: 5,087,617
[45] Date of Patent: Feb. 11, 1992

[54] METHODS AND COMPOSITIONS FOR TREATMENT OF CANCER USING OLIGONUCLEOTIDES

[75] Inventor: Larry J. Smith, Houston, Tex.

[73] Assignee: Board of Regents, The University of Texas System, Austin, Tex.

[21] Appl. No.: 311,096

[22] Filed: Feb. 15, 1989

[51] Int. Cl.$^5$ ............................................. A61K 31/70
[52] U.S. Cl. ................................................. 514/44
[58] Field of Search ..................................... 514/44

[56] References Cited

U.S. PATENT DOCUMENTS

| | | | |
|---|---|---|---|
| 4,107,937 | 8/1978 | Chmiel | 62/64 |
| 4,481,946 | 11/1984 | Altshuler et al. | 604/4 |
| 4,486,188 | 12/1984 | Altshuler et al. | 604/4 |

FOREIGN PATENT DOCUMENTS

| | | |
|---|---|---|
| 0288163 | of 1988 | European Pat. Off. . |
| 0263740 | 5/1988 | France . |
| 8703451 | 6/1987 | United Kingdom . |

OTHER PUBLICATIONS

Chang et al., *Lancet*, Feb. 8, 1986:294-295.
Dippold et al., *Proc. Natl. Sci. USA* 78:1695-1699 (1981).
Heikkliala et al., *Nature* 328:445-449 (1987).
Matlashewski et al., *Embo Journal* 3:3257-3262.
*Chemical Abstracts*, vol. 103, No. 11, 16 Sep. 1985, E. Harlow et al., Abstract 82693K.
*Chemical Abstracts*, vol. 108, No. 21, 23 May 1988, Wickstrom et al.
*Proc. Natl. Acad. Sci.* 84:1028-32 (1988), Wickstrom et al.
Munroe et al., Oncogene 2:621-624 (1988).
David et al., Oncogene 3:179-185 (1988).
Matsukura et al., Gene 72:343-347 (1988).
Levi and Ozato, Genes and Development 2:554-566 (1988).
Stein and Cohen, Cancer Research 48:2659-2668 (1988).
Matsukura et al., Proc. Natl. Acad. Sci. 84:7706-7710 (1987).
Lubbert et al., J. Med. 167:873-886 (1988).
Paoletti, Anti-Cancer Drug Design 2:325-331 (1988).
Cattoretti et al., British Journal of Cancer 57:353-357 (1988).
Yokoyama et al., Proc. Natl. Acad. Sci. USA 84:7363-7367 (1987).
Mercola et al., Biochemical and Biophysical Research Communications 147:288-294 (1987).
Nishikura and Murray, Molecular and Cellular Biology, 7:639-649 (1987).
Shohat et al., Oncogene 1:277-283 (1987).
Boyle and Gee, Cancer Investigation 5:113-118 (1987).
Rovinski et al., Molecular and Cellular Biology 7:847-853.
Kopelovich and Deleo, JNCL 77:1241 (1986).
Holt et al., Prop. Natl. Acad. Sci. 83:4794-4798 (1986).
Lamb and Crawford, Molecular and Cellular Biology, 6:1379-1385 (1986).
LaPlanche et al., Nucleic Acids Research 13:9081-9093 (1986).
Smith et al., J. Exp. Med. 164:751-761 (1986).
Kaczmarek et al., Exp. Cell Res. 162:268-272 (1986).
Nara and McCulloch, Leukemia Research 10:273-277 (1986).
Prokocimer et al., Blood 68:113-118 (1986).
Kim and Wold, Cell, 42:129-138 (1985).
Eliyahu et al., Nature 316:158-160 (1985).
Mowat et al., Nature 314:633-636 (1985).
Izant and Weintraub, Science 229:345-452 (1985).
Parada et al., Nature 312:649-651 (1984).
Izant and Weintraub, Cell, 36:1007-1015 (1984).
Mercer et al., Molecular and Cellular Biology 4:276-181 (1984).
McCulloch et al., Leukemia, vol. 2:12 (date of publ. unknown).
Curtis et al., J. Clinical Oncology 2:253-259 (1984).
McCulloch et al., Blood 59:601-608 (1982).
Mercer et al., Proc. Natl. Acad. Sci. 79:6309-6312 (1982).
Dialog Search.

*Primary Examiner*—John W. Rollins
*Attorney, Agent, or Firm*—Arnold, White & Durkee

[57] ABSTRACT

The present invention provides methods useful in autologous bone marrow transplantation and cancer therapy. According to one aspect of the invention, bone marrow cells from a patient having cancer are treated with selected antisense oligonucleotides in order to deplete the bone marrow of malignant cells prior to infusion back into the bone marrow donor. In a separate embodiment, selected antisense oligonucleotides are administered systemically for anticancer therapy.

26 Claims, No Drawings

METHODS AND COMPOSITIONS FOR TREATMENT OF CANCER USING OLIGONUCLEOTIDES

BACKGROUND OF THE INVENTION

Field of the Invention

The present invention relates to methods and compositions useful in cancer therapy. A preferred embodiment relates to the use of antisense oligonucleotides to purge tumor cells from bone marrow prior to autologous bone marrow transplantation. With this novel treatment, the bone marrow cells are obtained from an individual, and exposed to a proliferationinhibiting amount of an oligonucleotide having a sequence complementary to a sequence of RNA transcribed from a gene present in the cancerous cells. The cells are then infused back into the individual. This treatment preferentially inhibits the proliferation or kills malignant cells but not normal cells. Preferably, the gene encodes protein P53, although other antisense oligonucleotides may also be used. The invention also includes chemotherapeutic procedures and compositions for in vivo administration.

DESCRIPTION OF THE RELATED ART

This discussion illustrates the problems faced by clinical investigators seeking to improve cancer treatments. A number of references have been included for the convenience of the reader. Inclusion of these references is not an admission that such references represent prior art with respect to the present invention.

Cancer is one of the most feared diseases of our age, causing many thousands of deaths each year. Unfortunately, despite substantial advances in cancer therapy, significant room for improvement remains. Many of the antineoplastic agents currently used in cancer treatment have an unacceptably low therapeutic index; in other words, these agents are unable to block proliferation of or kill malignant cells at doses that do not cause unacceptable toxicity in normal tissue. Consequently, treatment with these agents causes undesirable side effects, and in many circumstances, an effective dose of these agents may even be fatal to the host. Therefore, for many years, cancer researchers have sought to develop a method for treating cancer that would allow one to selectively kill the cancer cells without destroying normal host tissue.

Autologous bone marrow transplantation (ABMT) represents a significant advance in this area. With this technique, one first removes bone marrow cells from an individual having cancer, and then extensively treats the patient with radiation, antineoplastic agents, or a combination of both at a dose sufficient to eliminate most, if not all, of the malignant cells. Unfortunately, this treatment often kills normal hemopoietic cells as well. As a result, it is necessary to reconstitute the patient's hemopoietic system by transplanting the marrow removed prior to treatment. This procedure has been described by Chang, et al. Lancet, pp. 294-295 (Feb. 8, 1986), and in a monograph entitled *Autologous Bone Transplantation: Proceedings of the Third International Symposium*, Dicke, et al., (eds), The University of Texas M.D. Anderson Hospital and Tumor Institute at Houston (1987), both of which are expressly incorporated herein by reference.

One major disadvantage associated with ABMT is the fact that cells of the bone marrow graft are often contaminated with malignant cells. This is particularly true when the patient suffers from a malignancy of the type known to invade or originate from bone marrow, for example, leukemias, lymphomas, myeloma, breast cancer, and small cell carcinoma of the lung.

Existing attempts to reduce or eliminate malignant cells from bone marrow involve the use of either monoclonal antibodies, drugs, or simple in vitro culture. However, these existing purging methods have well documented inherent shortcomings. For example, techniques that employ antibodies are dependent on the antigen density of the tumor cells, which may, in some cases, be quite low (Boyle and Gee, *Cancer Investigation* 5:113–118 (1987)). In addition, heterogenity of tumor antigens complicates selection of a monoclonal antibody that is specific for a given tumor. In one study, mafosfamide has been reported to be more effective than monoclonal antibodies for bone marrow purging prior to transplantation. However, despite this report that this procedure improved clinical outcome in patients with acute leukemia, the procedure was not curative. (Gorin, *Exp. Hemat.* 16:415 abstract 9, 1988). Other investigators report that there is a significant progressive shift from malignant to normal myelopoiesis when marrow from donors with acute or chronic myelocytic leukemia is maintained in culture up to about 4 weeks. This finding has led to attempts to purge marrow by in vitro culture (Coulumbel, et al., *J. Clin. Invest.* 75:961, 1985; Eaves, et al., *Haem. Blood Transfusion* 29:163, 1985) prior to autologous bone marrow transplantation. Although one group reports that this procedure appeared to cure one patient with acute myelogenous leukemia (Chang, et al., *Lancet* 1:2914, 1986), in general, the continuing presence of malignant hemopoiesis throughout the culture period limits the therapeutic value of this technique.

Recently, it has been learned that expression of certain genes involved in cellular proliferation can be inhibited by treating cells expressing those genes with "antisense" molecules. These antisense molecules have a sequence that is complementary to a portion of the RNA transcribed from the selected gene. Although the exact molecular mechanism of inhibition is not known, it has been suggested to result from formation of duplexes between the antisense molecule and RNA transcribed from the target gene. The duplexes may inhibit translation, processing, or transport of mRNA sequence or may lead to digestion by the enzyme RNaseH.

Very recent studies involving the use of antisense oligonucleotides have been reviewed by Stein and Cohen, *Cancer Res.* 48:2659 (1988). Several types of antisense molecules have been screened for their ability to inhibit the synthesis of particular proteins using both intact cells and in vitro systems for protein synthesis. See Paoletti, *Anti-Cancer Drug Design* 2:325 (1988). For example, agents with specificity for RNA transcribed from the myc gene have been reported to inhibit the proliferation of the human AML line HL60 (Wickstrom, et al., *Proc. Natl. Acad. Sci. USA* 85:1028 (1988) and normal T lymphocytes (Heikkila, et al., *Nature* 328:445 (1987), and oligodeoxynucleotides complementary to cyclin mRNA have been reported to suppress the division of 3T3 cells. (Jaskulski, et al. 1988). In addition, in a murine system, transfection of a plasmid encoding antisense p53 RNA into transformed MethA or non-tranformed NIH3T3 fibroblasts was reported to reduce the growth rate of the transfectants. Of course, studies in the mouse may have very limited applicability to human systems, particularly where, as with p53, significant differences exist between the structure of the murine gene and the human gene given the same designation. Lamb and Crawford *Mol. Cell Biol.* 6:1379 (1986).

Unfortunately, although many of the references cited above are of general scientific interest, they suffer from a number of shortcomings that render them insufficient to establish efficacy of oligonucleotides as chemotherapeutic agents for cancer. For example, none of the studies reported to date indicate that treatment with selected antisense oligonucleotides would be likely to have an acceptable therapeutic index. It has not been shown that antisense oligonucleotides are lethal for or even inhibitory for proliferation of malignant cells but not corresponding normal cells under the same treatment conditions. In addition, these studies do not describe the effects of antisense oligonucleotides on fresh tumor cells or fresh normal cells; instead, the studies utilized continuous cell lines which differ in many respects from fresh cells and whose relevance as a model for screening of chemotherapeutic agents has been repeatedly challenged by members of the scientific community. Vinditte, Seminars in Oncology Vol. 8, p. 349 (1981). Fortunately, with the present invention, these shortcomings have been overcome and the therapeutic potential of chemotherapy with selected antisense oligonucleotides convincingly established for the first time.

Moreover, the present inventor has now discovered that certain antisense oligonucleotides, and in particular, an oligonucleotide complementary to the mRNA encoding the human p53 gene product, may be successfully used to selectively eliminate malignant cells from bone marrow prior to autologous bone marrow transplantation. These and other advantages of the invention are described more fully below.

SUMMARY OF THE INVENTION

The present inventor has now discovered a new and unobvious method for treating bone marrow cells from an individual having cancer prior to infusion of the bone marrow cells back into the individual. This method comprises the following steps: obtaining bone marrow cells from the individual and exposing the bone marrow cells to a proliferation inhibiting amount of an oligonucleotide having a sequence complementary to a sequence of RNA transcribed from a target gene present in the cells of the cancer. Target genes suitable for use with the present invention are more completely described herein, for example, in the section entitled "Description of the Preferred Embodiments." However, in a preferred embodiment, the target gene will be a "traitor" gene of the type described more completely herein. In an additional preferred embodiment, the target gene is a gene encoding p53. In yet still another preferred embodiment, the proliferation inhibiting amount is approximately 10-200 micromolar.

In a related embodiment, the inventor has a provided a method for treating an individual having cancer comprising obtaining bone marrow cells from the individual, exposing the bone marrow cells to a proliferation inhibiting amount of an oligonucleotide having a sequence complementary to a sequence of RNA transcribed from a target gene present in the cells of the cancer, and transplanting the exposed cells into the individual. In a related embodiment, the individual so treated receives an additional preparation also containing oligonucleotides. The method of the present invention may be useful for treating any number of types of cancers, particularly those known to express p53 including cancer of cells of the hemopoietic system, for example leukemia, myelogenous leukemia, lymphoma, myeloma, as well as breast cancer, or gastrointestinal cancer.

The oligonucleotide selected may be any of a number of types, including those having a charged or uncharged backbone. Particularly preferred are the methylphosphonate oligonucleotides and the phosphorothioate oligonucleotides. Also preferred are oligonucleotides comprising at least eight bases and complimentary to a sequence of RNA located 5' to the initiation codon of the target gene. Additionally, the oligonucleotide may comprise at least eight bases and be located within forty bases of the initiation codon. Finally, the oligonucleotide may comprise the sequence 3'-GGTCTGACGGAAGGCCCAGTGACGGTA-5'.

Although the bone marrow cells may be exposed to the oligonucleotides under a variety of conditions, in a preferred embodiment, the exposing step will comprise the steps of fractionating the bone marrow cells to obtain a mononuclear cell fraction and culturing the mononuclear fraction together with a proliferation inhibiting amount of the oligonucleotide for at least about 1-10 days.

The invention also comprises a general method for killing of cancer cells. This method comprises exposing the cancer cells to a lethal amount of an oligonucleotide having a sequence complementary to a sequence of RNA transcribed from a target gene present in the cancer cells. In a preferred embodiment, the cancer cells will comprise cancer cells present in bone marrow. A number of suitable targets for use in connection with this aspect of the invention. Suitable targets may be determined, for example, by testing oligonucleotides complementary to RNA derived from such targets in accordance with the types of methods set forth by the inventor in the present application in which the potential for selective killing is determined by, comparing the effects of particular antisense oligonucleotides on fresh tumor cells and corresponding normal tissue (see, for example, Example 1). However, it should be appreciated, that with this aspect of the invention, it is important that the oligonucleotide selected, not only inhibit proliferation of, but selectively kill the cells of the tumor. An amount of oligonucleotide sufficient to achieve this end is considered to be a lethal amount. However, in a particular embodiment, a lethal amount is defined as an amount sufficient to allow one to achieve a serum concentration of oligonucleotides of about 30-200 micromolar, where the gene is p53.

In a related embodiment, the invention comprises a method for treating an individual having cancer, by administering to the individual a sufficient amount of a preparation contining oligonucleotides complementary to RNA transcribed from a target gene to kill the cancer cells in said individual. The methods described may be used to treat cancers of a number of types, including cancers of the cells of the hemopoietic system, for example leukemia, myeloid leukemia, lymphoma, myeloma, as well as breast cancer, carcinoma of the lung, gastrointestinal cancer.

With these embodiments of the invention, a number of types of oligonucleotides, including those having charged or uncharged backbones, such as methylphosphonate or phosphorothioate oligonucleotides may be used. However, uncharged oligonucleotides, may be preferred. The oligonucleotides may comprise at least 8 bases and be complimentary to a sequence of RNA located 5' to the initiation codon of the RNA transcript. Alternatively, the oligonucleotide may comprise at least 8 bases and be located within 40 bases of the initiation codon of said transcript. In a specific embodiment, the oligonucleotide will comprise the sequence 3'-GGTCTGACGGAAGGCCCAGTGACG-GTAC-5'. Finally, the invention comprises pharmaceutical compositions for inhibiting proliferation of malignant cells, including compositions comprising oligonucleotides complimentary to mRNA transcribed from the p53 gene.

With these methods and compositions, striking increases in the efficacy of bone marrow purging for autologous bone marrow transplantation, and in cancer chemotherapy in general, can be achieved. The advantages of the present invention will become more apparent from detailed description of the preferred embodiments and from examples set forth herein. These examples and discussion are intended to be illustrative but exhaustive.

DESCRIPTION OF THE PREFERRED EMBODIMENTS

A preferred embodiment of the present invention relates to use of antisense oligonucleotides to deplete or substantially deplete bone marrow of malignant cells prior to autologous bone marrow transplantation. The selected antisense oligonucleotides have a sequence that is complementary or substantially complementary to a sequence of RNA transcribed from a gene that when blocked will preferentially inhibit the growth of or kill malignant cells as compared to normal cells. In a preferred embodiment, the oligonucleotide will be complementary to mRNA transcribed from the human gene encoding a protein known as p53.

However, as the following discussion indicates, oligonucleotides complementary to mRNA transcribed from other genes crucial to cell viability may also be targeted for inhibition with antisense oligonucleotides. Higher organisms have an elaborate system of interactive mechanisms that are responsible for determining the size, position and architecture of their component tissues. Such regulation requires that coordinating information be communicated between cells across variable distances. This is accomplished, at least in part, by an array of information carrying molecules that include elements of the endocrine and paracrine systems as well as cell surface components that act through cell-cell contact. Of particular interest are those informational molecules that deliver directions concerning the maintenance of cell viability and regulate cellular proliferation and differentiation.

Individual cells detect, interpret and act upon this exogenous information by means of complex afferent sensory and efferent response systems, the components of which include receptors for the exogenously derived informational molecules, secondary messengers and transcriptional and translational regulators. Hence, when a cell is presented with a particular set of informational molecules and an interpretation made, the latter is manifested, at least in part, in terms of an appropriate pattern of gene expression that is required for obtaining an appropriate response. Such patterns could be thought of as being "cooperative patterns."

The behavior of neoplastic cells suggests that they are somehow aberrent with respect to these mechanisms (Weinstein, J. Cell. Biochem. 33, 213, 1987), and a variety of specific tumor associated changes have been described for particular components of these mechanisms in tumor cells. Therefore, it is believed that the sensory component of malignant cells may respond to environmentally derived cues by providing for an "uncooperative pattern" of gene expression that in turn provides for the malignant phenotype.

Both normal and malignant primary (fresh) cells die if placed in a significantly abnormal environment in vivo or in vitro, even when provided with all the necessary nutrients and physical conditions necessary to maintain cellular functions. Primary malignant cells typically can tolerate a somewhat broader range of environments than normal cells, but the range is still highly restricted. It appears then that primary normal or malignant cells are programmed to die if deprived of environmentally derived informational molecules that instruct them to survive.

The present inventor has found that antisense p53 oligonucleotides can inhibit the proliferation of and ultimately kill primary human leukemic blasts while not producing similar effects on fresh normal bone marrow cells. This unobvious result indicates that the interactive mechanisms for detecting, interpreting and responding to environmental informational molecules involved in regulating cell proliferation and viability in malignant cells are so altered from normal in terms of their dynamic interactions (involving signal transduction and interpretation) that the inhibition of a single gene or set of genes coding for proteins involved in this process by antisense oligonucleotides is sufficient to change the impact of the informational molecules so a cellular death or growth inhibition program can be selectively instituted in the malignant cells. The term "traitor genes" is used herein to describe those genes in malignant cells that may be suitable for targeting for inhibition with antisense molecules in accordance with the invention that will result in growth inhibition or killing of malignant cells but not their normal counterparts over a selected dose range. Suitable target or traitor genes may themselves either be functionally abnormal or be normal but function to maintain the viability and proliferation of malignant cells as part of an abnormal pattern of gene expression. However, since simple growth inhibition of malignant cells that lasts only during exposure to antisense oligonucleotides would not be adequate for systemic treatment, with respect to this aspect of the invention, it is particularly significant that the present inventor has been able to document selective killing of malignant cells.

Since the targeted traitor genes include genes that are crucial for the maintenance of viability and for proliferation of malignant cells their products may fall into certain categories. These include informational molecules that carry instructions dealing with cell proliferation, viability, and differentiation as well as their receptors; second messenger molecules which are involved in signal transduction and most likely its interpretation; and transcriptional and translational regulators that respond to such information by providing for a particular pattern of gene expression at the RNA and protein levels. The following is a partial listing of potential target or "traitor" genes that may be suitable for use in accordance with the present invention. Informational molecules that normally have an exogenous source are included because neoplastic cells may sometimes elaborate such molecules which may have an autostimulatory effect. Regulations of cellular differentiation are mentioned because differentiation and proliferation potential are often coupled and are inversely related. Where the molecule listed is not a protein, the appropriate target genes would encode enzymes that are involved in the synthesis, breakdown or modification of the indicated molecule.

| Potentially Useful Target Genes For Bone Marrow Purging | |
|---|---|
| Epidermal growth factor and its receptor | Carpenter and Cohen Ann. Rev. Biochem. 48, 193, 1979 |
| Platelet derived growth factor and its receptor | Heldin and Westermark Cell 37, 9, 1984 |
| Transforming growth factor and its receptor | Sporn, et al. Sci. 233, 532, 1986 |
| Endorphins and their receptors | Brummitt et al. "Monokines and other Non-lymphocytic Cytokines p. 125, Alan R. Liss, 1988 |
| abl and bcr/abl (ligand not defined) | Konopka and Witte Biochem Biophys Acta 823, 1, 1985. |
| Hematopoietic growth factors (including G-CSF, GM-CSF, M-CSF and IL 1-6) and their receptors | Clark and Kamen Sci. 236, 1229, 1987. |
| Tumor necrosis factor and its receptor | Murase et al. Blood 69, 467, 1987 |
| Aproliferin and its receptor | Wier and Scott A.J.P. 125, 546, 1986 |
| Leukemia Inhibitory Factor and it receptor | Moreau et al. Nature 336, 690, 1988 |
| cyclic nucleotides and calmodulin | Rasmussen, H. "Calcium and cAMP As Synarchic Messengers" Wiley, N.Y., 1981 |
| diacylglycerol; protein kinase C | Alkon and Rasmussen Sci. 239, 998, 1988 |
| polyamines | O'Conor et al. Cell Tissue Kinet. 19, 539, 1986 |
| Metabolites of Arachidonic Acid (leukotrienes and prostaglandins) | Snyder et al. Exp. Hematol, 17, 6, 1989. |
| Interferon | Rigby et al. Blood 65, 858, 1985. |
| ADP-ribosylases | Daniel and Dexter Leukemia 2, 523, 1988. |
| phosphatidylinositol | Faletto et al. Cell 43, 315, 1985. |
| Guanosine triphosphatase. | Varmus and Bishop Cancer Surveys 5, No. 2, 1986. |
| protein phosphases | Weinstein, J. Cell. Biochem. 33, 213, 1987. |
| protein kinase A | Weinstein, J. Cell. Biochem. 33, 213, 1987. |
| phospholipases | Weinstein, J. Cell. Biochem. 33, 213, 1987. |
| protein kinase G | Weinstein, J. Cell. Biochem. 33, 213, 1987. |
| actin | Weinstein, J. Cell. Biochem. 33, 213, 1987. |
| phospholipase inhibitors (such as lipocortin) | Weinstein, J. Cell. Biochem. 33, 213, 1987. |
| p53 | Mercer and Baserga Exp. Cell Res. 160, 31, 1985 |
| AP1 | Bohmann et al. Sci. 238, 1386, 1987 |
| Steroid Receptors | Schule et al. Sci. 242, 1418, 1988 |
| FOS | Sassone-Corsi et al. Cell 54, 553, 1988 |
| p39 | Sassone-Corsi et al. Cell 54, 553, 1988 |
| JUN | Sassone-Corsi et al. Cell 54, 553, 1988 |
| Cyclin | Mathews et al. Nature 309, 374, 1984 |
| MYC | Nau et al. Nature 318, 69, 1985 |
| poly ADP ribosylase | Singh et al. Carcinogenesis 6, 1489, 1985. |
| CDC2Hs | Lee et al. Nature 333, 676, 1988 |
| Myb | Pierce et al. Clinics in Haemat. 15, 573, 1986 |
| MOS | Pierce et al. Clinics in Haemat. 15, 573, 1986. |
| R1 and R2 | Zinn and Maniatis Cell 45, 611, 1986 |
| SRF | Treisman EMBO J. 6, 2711, 1987 |

Accordingly, separate embodiments of the invention comprise methods for (1) bone marrow purging and (2) in vivo chemotherapy. Particularly for both embodiments preferred are oligonucleotides directed against the gene encoding p53.

I. USE OF SELECTED ANTISENSE OLIGONUCLEOTIDES FOR DEPLETING MALIGNANT CELLS FROM BONE MARROW

Described below is a model system for removing malignant cells from bone marrow by treating the bone marrow cells with selected antisense oligonucleotides. The inventor's previously unappreciated discovery that selected antisense oligonucleotides are toxic for cells of the tumor but not for normal bone marrow cells provides a strong experimental basis for application of the method in autologous bone marrow transplantation.

Patients for whom the methods of the present invention may prove most efficacious include those having cancers of the hematopoietic system, breast cancer and gastro-intestinal cancer. The former category of diseases includes, but is not limited to, various forms of lymphoma and leukemia as well as multiple myeloma.

Pursuant to the invention, one first obtains a sample of bone marrow from the patient in accordance with any of a number of standard techniques, including aspiration from the illiac crest of a donor, for example, as described in U.S. Pat. No. 4,481,946 and U.S. Pat. No. 4,486,188. The patient may then be treated with an optimal dose of radiation or chemotherapy as previously described in Autologous Bone Transplantation: Proceedings of the Third International Symposium, Kicke, et al., (eds) The University of Texas M.D. Anderson Hospital and Tumor Institute at Houston (1987).

The bone marrow sample may be frozen and stored until needed, for example, as described in U.S. Pat. No. 4,107,937 and U.S. Pat. No. 4,117,881, or immediately treated with the oligonucleotide as described more fully below.

One of the most important parameters affecting practice of the present invention is the RNA sequence to which the antisense oligonucleotide is directed (target RNA). The oligonucleotide may be targeted to RNA transcribed from any of the number of selected target genes that have been discussed above, so long as the oligonucleotide kills or inhibits growth of malignant cells but is not so toxic for normal tissue as to prevent one from obtaining an acceptable therapeutic index. Suitable oligonucleotides may be identified with the aid of the present disclosure by testing for differential toxicity, for example, as described in Example I below. Moreover, as indicated above, suitable targets may be those encoding cell surface receptors, modulators of intracellular messengers, transcriptional regulators and effector genes that regulates cell proliferation, differentiation and viability. A commercially available database (Genebank) includes a large number of genetic sequences which may be used to design oligonucleotides suitable for practice of the invention. Accordingly, those sequences are considered to be incorporated herein by reference.

However, the present inventor has discovered that an oligodeoxynucleotide complementary to the mRNA transcribed from the p53 gene is surprisingly effective for practice of the present invention. This gene has been implicated in regulation of cell proliferation and of gene expression. Mercer et al., *Proc. Natl. Acad. Sci. USA* 79:6309–6312 (1982); Mercer, et al. *Mol. Cell. Biol.* 4:276–281 (1984). Its expression is not restricted to tumor cell lines; fresh human tumor cells from patients with colorectal and mammary tumors have also exhibited elevated expression of the p53 gene product. Previously, the present inventor was able to detect p53 protein synthesis in acute myeloblastic leukemia cells but was not able to detect it in normal cells from bone marrow using a metabolic labeling assay. (Smith, et al., *J. Exp. Med.* 164:751 (1986). In accordance with the present invention, the inventor has now shown that antisense oligonucleotides complementary to p53 mRNA exhibit selective toxicity for malignant cells but do not inhibit growth of normal bone marrow cells. These studies are briefly described below in Example I.

As a general matter, the oligonucleotide employed will have a sequence that is complementary to the sequence of the target RNA. However, absolute complementarity is not required; in general, any oligonucleotide having sufficient complementarity to form a stable duplex with the target RNA is considered to be suitable. Since stable duplex formation depends on the sequence and length of the hybridizing oligonucleotide and the degree of complementarity between the antisense oligonucleotide and the target sequence, the system can tolerate less fidelity (complementarity) when longer oligonucleotides are used. However, it presently believed that oligonucleotides of about 8 to 40 bases in length and having sufficient complementarity to form a duplex having a melting temperature of greater than about 40° C. under physiologic conditions are particularly well suited for practice of the invention. Thoung et al. PNAS USA 84. 5129, 1987; Wilson et al; *Nucleic Acids Res.* 16:5137 (1988). Accordingly, such oligonucleotides are preferred.

Yet another variable that may affect practice of the invention is the region of the target RNA to which the selected oligonucleotide is designed to hybridize. Although oligonucleotides capable of stably hybridizing with any region of the RNA may be suitable for practice of the invention, the present inventor has discovered that oligonucleotides complementary to a region including the initiation codon are particularly effective.

The most preferred oligonucleotides are those having a sequence complementary to the initiation codon and extending about 5 to 37 bases upstream (in the 5' direction) therefrom. Most preferred is an oligonucleotide extending about 25 bases upstream from the initiation codon.

The oligonucleotide employed may represent an unmodified oligonucleotide or an oligonucleotide analog. Suitable analogs include but are not limited to the ethyl or methyl phosphonate analogs disclosed by U.S. Pat. No. 4,469,863 and the phosphorothioate modified oligodeoxynucleotides described by LaPlanche, et al., *Nucleic Acids Research* 14:9081 (1986) and by Stec. et al. *J. Am. Chem. Soc.* 106:6077 (1984). Furthermore, recent advances in the production of oligoribonucleotide analogues mean that other agents may also be used for the purposes described here, e.g., 2'-methylribonucleotides (Inoue et al., Nucleic Acids Res. 15, 6131, 1987) and chimeric oligonucleotides that are composite RNA-DNA analogues (Inoue et al. FEBS Lett. 215, 327, 1987). The most highly preferred oligodeoxynucleotides are synthesized according to the procedure of Matsukura, et al. *Gene* 72, 343, 1988.

Of course, in order for the tumor cell targets to be effectively inhibited or poisoned by the selected antisense oligonucleotides, the cells must be exposed to the oligonucleotides under conditions that facilitate their uptake by the malignant cells. This may be accomplished by a number of procedures, including, for example, simple incubation of the cells with the oligonucleotides in a suitable nutrient medium for a period of time suitable to achieve selective inhibition of the malignant cells. The present inventor has discovered that culture of the bone marrow with selected oligonucleotides (antisense p53 oligonucleotides, in the example) inhibits proliferation of cells after 8 hours exposure (and possibly sooner). Incubation for at least about 7–10 days kills fresh malignant cells (leukemic blasts, in the example) but has no significant effect on fresh cells from normal bone marrow. Accordingly, a preferred procedure for practice of the invention involves placing the bone marrow cells into culture, for example, as described by Gartner and Kaplan, *Proc. Natl. Acad. Sci. USA* 77:4756 (1980); Coulombel, et al., *Blood* 67:842 (1986); Meagher, et al. *Blood* 72:273 (1988) or U.S. Pat. No. 4,721,096 with an optimal concentration of the selected antisense oligonucleotide.

The concentration of oligonucleotide to be used may vary, depending upon a number of factors, including the type of cancerous cells present in the marrow, the type, and the specificity of the particular antisense oligonucleotide(s) selected, and the relative toxicity of the oligonucleotide for malignant and normal bone marrow cells. Although the present inventor has observed significant inhibition of tumor cell DNA synthesis at oligonucleotide concentrations as low as 30 micromolar, optimal inhibition was observed at concentrations of at least 60 micromolar in the model system described below. With the aid of the techniques set forth in the present disclosure, those of skill in the art should be able to determine the optimal concentration to be used in a given case.

After the marrow cells have been exposed to the oligonucleotide and, in some cases, cultured as described above, they are then infused into the transplant recipient to restore hemopoiesis.

EXAMPLE 1

Ability Of p53 Oligonucleotides To Selectively Inhibit Proliferation Of Malignant Cells In Vitro The following example demonstrates the ability of p53 antisense oligonucleotides to inhibit proliferation of fresh human myeloid leukemia cells in a model system utilizing tritiated thymidine uptake as a measure of cellular proliferation.

A. Oligodeoxynucleotides

The particular oligodeoxynucleotide used for the experiments below was a 28 base phosphorothioate modified oligodeoxynucleotide complementary to the AUG initiation codon and the 25 bases located adjacent and 5' to same. This oligonucleotide has the sequence and 3'-GGTCTGACGGAAGGCCCAGTGACG-GTAC-5'is referred to herein as antisense p53 ODN(1).

The corresponding sense oligodeoxynucleotide having the sequence 5'-CCAGACTGCCTTCCGGGT-CACTGCCATG-3'was used as a control. This oligodeoxynucleotide is referred to herein as sense p53 ODN(1). The oligodeoxynucleotides (ODN) were synthesized and purified according to published procedures (Matsukura, et al., Gene 72:343 (1988)) at Applied Biosystems, Inc., 777 Lincoln Center Drive, Foster City California. Prior to use, the oligonucleotide (ODN) preparation was dissolved in a small amount of autoclaved distilled water. Alpha minimal essential medium (minus nucleotides and nucleosides) was then added to make a 100 micromolar stock solution of each of the selected oligonucleotides. The stocks were stored at −70° C.

B. Cells and Cell Culture

Leukemic blast cells were obtained from the peripheral blood of two patients with acute myelogenous leukemia with high blast counts. Normal bone marrow specimens were obtained from illiac crest of two donors by standard procedures. Each set of samples was diluted 1:3 with phosphate buffered saline and the mononuclear cells isolated by a ficoll hypaque (d=1.077) centrifugation step. T lymphocytes were removed by a second centrifugation with the density fractionation medium after rosetting with sheep red blood cells as previously described (Minden et al., Blood 54:186 (1979)). Greater than 95% of the patient cells obtained after T lymphocyte depletion had a blast morphology.

Prior to testing in the tritiated thymidine ($^3$HTdr) uptake assay, the normal bone marrow mononuclear cells were stimulated with growth factors for three days to ensure that the maximum number of cells would be in cycle when exposed to the ODNs. Briefly, the cells were cultured in the presence of Alpha MEM, 20% fetal calf serum, and 10% 5637 bladder cell carcinoma line conditioned medium (5637 CM), at an initial cell density of $5 \times 10^5$ cells per ml. The 5637 CM is a source of hematopoietic growth factors including IL-1, GM-CS, and G-CSF and was prepared as described by Hoang and McCulloch, Blood 67:748 (1985). The cultures were incubated at 37° C. in 5% $CO_2$ in air.

In some experiments, normal bone marrow mononuclear cells or leukemic blast cells were cultured under the same conditions for variable lengths of time in the presence of ODNs. Aliquots were then taken at various times for the $^3$HTdR assay to determine the kinetics of inhibition.

C. $^3$HTdR Assay

Cellular proliferation was monitored by $^3$HTdR uptake essentially as described by McCulloch and Till, Blood 9:269 (1977). Each variable was determined in triplicate. Leukemic blasts or normal bone marrow mononuclear cells were initially suspended in Alpha MEM at $10^7$ cells per ml. An aliquot of these cells received 1000 rads over 0.56 minutes from a cesium source for use as a control to determine background counts. Both irradiated and unirradiated cells were cultured in flat bottom 96 well plates at a density of 2 or $1 \times 10^5$ cells in a volume of 0.2 ml consisting of Alpha MEM, 10% FCS, and 10% 5637 CM dialyzed to remove thymidine. Additional cultures of unirradiated cells containing varying amounts of antisense p53 ODN(l) or corresponding sense p53 ODN(1) were prepared under the same conditions. The cultures were incubated at 37° C. in 5% $CO_2$ in air for time periods described. They were then pulsed with 1 microcurie per well of 3HTdR for 4 hours, and the cells were harvested on 2.4 cm Whatman GF/C filters using a suction manifold. The filters were then rinsed in turn with 50 ml volumes of saline, 5% trichloroacetic acid in distilled water and 95% ethanol (Fisher). The dry filters were then placed in scintillation vials with 5 ml of Formula-963 (Dupont) scintillation fluid. Finally, counts were determined and the means for each condition compared using one way analysis of variance.

D. Experimental Results

In the initial test of the system, blasts from patient #1 were incubated in microwells for 18 hours in the presence or absence of 30 micromolar antisense p53 ODN(1) and then assayed for tritiated thymidine uptake. The results, shown in Table 1 below, indicate that the antisense oligonucleotide caused significant inhibition of tritiated thymidine uptake. The mean CPM for the irradiated cells was 1234.

TABLE 1

| Antisense p53 ODN(1) Concentration | Mean CPM | % Inhibition | P Value |
|---|---|---|---|
| 0 micromolar | 34419 | — | — |
| 30 micromolar | 23189 | 33 | 0.012 |

A second experiment was performed essentially as described above except that the concentration of antisense p 53 ODN(1) was varied. In this experiment (Table 2), inhibition of tritiated thymidine uptake occurred at the highest concentration of ODN tested. The mean CPM for irradiated cells was 3802.

TABLE 2

| Antisense p53 ODN Concentration | Mean CPM | % Inhibition | P Value |
|---|---|---|---|
| 0 micromolar | 75792 | — | — |
| 5 micromolar | 86338 | N.S. | 0.273 |
| 10 micromolar | 93188 | 19 (stimulation) | 0.046 |
| 30 micromolar | 59174 | N.S. | 0.145 |
| 60 micromolar | 32831 | 57 | 0.002 |

N.S. = not significantly different from the untreated control

In yet another experiment, blasts from patient #1 were cultured for a prolonged period in the presence or absence of 30 micromolar antisense p53 ODN(1) and periodically sampled for testing in the $^3$HTdR assay. (Table 3) At the end of 7 days, the cultures were inspected with an inverted phase microscope. All of the cells in the antisense ODN treated cultures were dead and disintegrating. Although the cultures were continued several more days, there continued to be no sign of viable cells, and the tissue culture medium retained its normal color. The control culture, however, remained healthy and had to be placed with fresh medium on day 7. By this time, its medium had turned a yellowish orange color, an indication of active metabolism by the cultured cells.

There was no significant difference in tritiated thymidine uptake exhibited by control cultures assayed at different time points after initiation of culture. However, with the treated group, tritiated thymidine uptake observed after 24 hours of culture was significantly lower than the 8-hour value ($p<0.001$) or 48-hour value $p<0.003$). The 96-hour value was significantly lower than the 48-hour value ($p<0.0003$). Mean CPM for irradiated cells was 1234. The results of cell counts are shown in Table 4. However, the bulk of the cells in a fresh leukemia sample are proliferatively inert; hence, cell counts are not a very sensitive measure of cell proliferation.

TABLE 3

Patient #1
Mean CPM/% Inhibition /P Value at Different Times in Hours

| Antisense p53 ODN Concentration | 8 | | | 24 | | | 48 | | | 96 | | |
|---|---|---|---|---|---|---|---|---|---|---|---|---|
| | CPM | % | P | CPM | % | P | CPM | % | P | CPM | % | P |
| 0 micromolar | 40806 | | | 35560 | | | 41695 | | | 48509 | | |
| 30 micromolar | 30730 | 25 | 0.002 | 16709 | 53 | 0.002 | 25084 | 40 | 0.006 | 17922 | 63 | 0.005 |

TABLE 4

| | Cell Counts × 10$^5$ per ml time in hours | | | |
|---|---|---|---|---|
| Antisense p53 ODN concentration | 8 | 24 | 48 | 96 |
| 0 micromolar | ND | ND | 8.8 | 9.3 |
| 30 micromolar | ND | ND | 6.2 | 5.3 |

A third experiment was performed using the same conditions as set forth in the experiment described above except that the leukemia cells tested were obtained from a different donor (Patient #2) and the sense ODN was used as an additional control. The results of this experiment (Table 5) showed that proliferation of tumor cells was significantly inhibited by 30 to 60 micromolar antisense oligonucleotide but not by 60 micromolar sense oligonucleotide control. Irradiated cell mean CPM was 3585.

TABLE 5

| ODN(1) Concentration* (Micromolar) | Mean CPM | % Inhibition | P Value |
|---|---|---|---|
| 0 | 49822 | — | — |
| 5 a.s. | 52640 | N.S | 0.192 |
| 10 a.s. | 49161 | N.S. | 0.760 |
| 30 a.s. | 39353 | 21 | 0.001 |
| 60 a.s. | 28285 | 43 | <0.001 |
| 60 s. | 48943 | N.S. | 0.637 |

*a.s. = antisense
s. = sense
N.S. = not significantly different from untreated control A final experiment was performed essentially as described immediately above. However, in this experiment, the leukemic cells were obtained from a second donor and two normal bone marrow specimens that had been stimulated with 5637-CM for three days (as described in Section B) were used. Leukemic blast cells have previously been shown to generally exhibit density requirements of $>2\times10^5$/ml. for continued growth, Hoang and McCulloch, Leukemia. Res. 10:273 (1986). A sense p53 oligodeoxynucleotide was included as a control in all three sets of cultures. The normal bone marrow cultures were fed on day 7 by removing one-half of the culture medium and adding one-half volume of fresh medium. By day 10, the vast majority of leukemic blast cells in the culture receiving the antisense oligodeoxynucleotide, but not the sense oligodeoxynucleotide, were determined to be dead by examination with a phase microscopy and by their failure to proliferate and exhaust the culture medium. Neither treatment exhibited any significant toxicity for the normal bone marrow cells which were observed for 10 days with one feeding as described. Thus, this experiment confirmed the selective toxicity of the antisense oligodeoxynucleotide for malignant cells.

Tritiated thymidine uptake observed after 24, 48, and 96 hours of culture with either the sense or antisense oligodeoxynucleotides for both sets of cultures are reported in Tables 6 and 7 below and also demonstrates selective inhibition of the antisense oligonucleotides for malignant cells.

TABLE 6

Mean CPM/% Inhibition/P Value at Different Times in Hours

| p53 ODN Concentration* (Micromolar) | 24 | | | 48 | | | 96 | | |
|---|---|---|---|---|---|---|---|---|---|
| | CPM | % | P | CPM | % | P | CPM | % | P |
| 0 | 20287 | | | 23351 | | | 16741 | | |
| 30 a.s. | 13568 | N.S. | 0.084 | 11292 | 52 | 0.007 | 5201 | 69 | 0.004 |
| 30 s. | 15881 | N.S. | 0.149 | 17224 | N.S. | 0.099 | 20581 | N.S. | 0.051 |

*a.s. = antisense
s. = sense
N.S. = not significantly different from 0 micromolar

TABLE 7

Normal Bone Marrow
Mean CPM Donors 1 and 2 at Different Times in Hours

| p53 ODN Concentration | 24 | | 48 | | 96 | |
|---|---|---|---|---|---|---|
| | 1 | 2 | 1 | 2 | 1 | 2 |
| 0 | 17200 | 17913 | 22072 | 21578 | 10188 | 9595 |
| 30 a.s. | 20125 | 16745 | 24014 | 19996 | 9328 | 14766 |
| 30 s. | 18269 | 16891 | 24382 | 19422 | 11688 | 15473 | a.s. = Antisense
s. = Sense
Only mean counts per minute are given since for any given time point none of the results were significantly different from the untreated control except at 96 hours 30 micromolar sense ODN is significantly higher than the untreated control p = 0.012.

EXAMPLE 2

Use of Oligodeoxynucleotides In Autologous Bone Marrow Transplantation

The following prophetic example describes use of the present invention to purge malignant cells from bone marrow in a selected cancer patient.

Bone marrow is aspirated from the illiac crest of a cancer patient and the mononuclear cells fraction obtained by centrifugation over a gradient of ficoll-hypaque (d=1.077). Bone marrow mononuclear cells are resuspended of a density of about $1 \times 10^7$ cells per ml in a culture medium comprising MEM (Gibco) supplemented with a source of growth factors (such as 5637 CM) $5 \times 10^{-6}$ mol/l hydrocortisone hemisuccinate, 0.25 mg/ml catalase, 2 mmol/L mannitol (all 3 Sigma), 1% sodium pyruvate solution (100X), 1% vitamin solution (100×10.8% amino acid solution), (50X), 0.4% nonessential amino acid solution (200X), a 1% L-glutamine (200 mmole/l), (all purchased from Gibco), 12.5% horse serum (Hyclone), 12.5% FCS (Gibco) and 60 micromolar of antisense p53 ODN(1). Suspensions are placed in suitable culture vessels and and incubated at 37° in 5% $CO_2$ in air. The culture is fed at suitable periods by a complete media change and by removing a proportion of the nonadherent cells corresponding to the amount of growth. Generally, the culture will be harvested before the expiration of about 10 days.

As an optional step, the cells may be assayed at the end of the culture period to determine the number or percentage, if any, of malignant cells remaining after treatment with the oligonucleotides. Suitable assay procedures include karyotype analysis where the malignant cells have a characteristic karyotype such as the Philadelphia chromosome or those described by Watson and Duff, *Enzymology* 58:322 (1979) and by Sloane, et al., *Br. J. Cancer* 44:85 (1981).

After a culture period suitable to deplete at least a majority of the malignant cells from the marrow suspension (generally about 10 days), the cells are harvested from culture and infused into the recipient as previously described, *Autologous Bone Marrow Transplantation.* Dicke, Spitzer, and Jagannath (eds.) The University of Texas, M.D. Anderson Hospital and Tumor Institute at Houston, 1987. As an optional step, the patient may receive supplemental therapy with a pharmaceutical preparation comprising the selected antisense oligonucleotide used for bone marrow purging or, alternatively, a second antisense oligonucleotide preparation.

II. USE OF ANTISENSE p53 OLIGONUCLEOTIDES TO INHIBIT PROLIFERATION OF MALIGNANT CELLS IN VIVO

In addition to their utility for purging malignant cells from bone marrow prior to transplantation, the antisense oligonucleotides of the present invention may also find significant clinical utility as chemotherapeutic agents for treatment of a number of tumors including, for example gastrointestinal cancer, breast cancer, and cancers of blood. The antisense p53 oligonucleotides may prove particularly useful when administered to recipients of antisense p53 oligonucleotide-purged bone marrow transplants.

Several of the parameters that are listed below are related to selection of the particular oligonucleotide sequence to be used for purging of bone marrow also apply to the selection of the particular antisense oligonucleotide to be used as a chemotherapeutic agent in vivo. For example, as with antisense oligonucleotides used for bone marrow purging, absolute complementarity to the target gene sequence is not required. Instead a degree of complementarity sufficient to allow stable hybridization with the selected RNA target is considered suitable. Moreover, oligonucleotides of varying lengths may be employed; however, oligonucleotides having from about 8 to about 40 bases are preferred. Although the antisense oligonucleotide may be complementary to virtually any stretch of sequence within the target gene, antisense oligonucleotides complementary to the initiation codon and bases extending in the 5' direction therefrom, may be preferred. Oligonucleotides complementary to RNA encoding p53 are particularly preferred. The complete sequence of the p53 gene set forth by Lamb and Crawford, *Molecular and Cellular Biology* 6:1379-1385 (1986) and incorporated herein by reference may be of assistance in designing antisense sequences suitable for practice of the present invention. However, the sequence 3'-GGTCTGACG-GAAGGCCCAGTGACGGTAC-5'is preferred.

The antisense oligonucleotide selected for practice of the invention may be any of the types described by Stein and Cohen, *Cancer Research* 48:2569-2668 (1988), and including without limitation, unmodified oligodeoxynucleotides, ethyl-or methyl-phosphonate modified oligodeoxynucleotides, phosphorothioate modified oligonucleotides, dithioates, as well as other oligonucleotide analogs, including those incorporating ribozyme structures, and oligoribonucleotides such as those described by Inove et al., *Nucleic Acids Res.* 15:6131 (1987); and Chimeic oligonucleotides that are composite RNA, DNA analogues (Inove, et al., *FEBS Lett.* 2115:327 (1987). Oligonucleotides having a lipophillic backbone, for example, methylphosphonate analogs with ribozyme structures, may prove advantageous in certain circumstances; these molecules may have a longer half-life in vivo since the lipophilic structure may reduce the rate of renal clearance while the ribozyme structure promotes cleavage of the target RNA. Gerlach, *Nature* 334:585 (1988).

The oligonucleotides may be formulated into pharmaceutical compositions and administered using a therapeutic regimen compatible with the particular formulation. As described further below, with the aid of present disclosure, those of skill in the chemotherapeutic arts should be able to derive suitable dosages and schedules of administration for any of a number of suitable compositions that contain the compounds. Thus, pharmaceutical compositions within the scope of the present invention include compositions where the active ingredient is contained in an effective amount to kill the cells of the cancer without causing unacceptable toxicity for the patient. However, a preferred dosage comprises that which is sufficient to achieve an effective blood concentration of about 10 to 200 micromolar. Although a preferred range has been described above, determination of the effective amounts for treatment of each type of tumor may be determined by those of skill in the art of chemotherapeutic administration.

In addition to the antisense oligonucleotide compounds, the pharmaceutical compositions of the invention may contain any of a number of suitable excipients and auxiliaries which facilitate processing of the active compounds into preparations that can be used pharmaceutically. Preferably, the preparations will be designed for parenteral administration. However, compositions designed for oral or rectal administration are also considered to fall within the scope of the present invention. Preferred compositions will comprise from about 0.1 to about 1% by weight of the active ingredients.

Suitable formulations for parenteral administration include aqueous solutions of the active compounds in water-soluble or water-dispersible form. Alternatively, suspensions of the active compounds may be administered in suitable lipophilic carriers. The formulations may contain substances which increase viscosity, for example, sodium carboxymethyl cellulose, sorbitol, and/or dextran. Optionally, the formulation may also contain stabilizers.

Additionally, the compounds of the present invention may also be administered encapsulated in liposomes. The oligonucleotide, depending upon it solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

While the present invention has been described in conjunction with a preferred embodiment and specific examples, the description is not meant to limit it. One of ordinary skill, with the aid of the present disclosure, may be able to effect various changes, substitutions of equivalents and other alterations to the methods and compositions set forth. Therefore, the protection granted by Letters Patent should not be limited except by the language of the claims as set forth below.

What is claimed is:

1. A method for treating bone marrow cells from an individual having cancer prior to infusion of the bone marrow cells back into the individual, comprising the steps of:
    a) obtaining bone marrow cells from the individual; and
    b) exposing the bone marrow cells to a proliferation inhibiting amount of an antisense oligonucleotide having a sequence complementary to a sequence of RNA transcribed from a target gene present in the cells of the cancer, wherein said target gene is selected from the group consisting of those genes encoding cell surface receptors, modulators of intracellular messengers, or transcriptional regulators.

2. A method for treating an individual having cancer comprising the steps of:
    a) obtaining bone marrow cells from the individual; and
    b) exposing the bone marrow cells to a proliferation inhibiting amount of an antisense oligonucleotide having a sequence complementary to a sequence of RNA transcribed from a target gene present in the cells of the cancer, wherein said target gene is selected from the group consisting of those genes encoding cell surface receptors, modulators of intracellular messengers, or transcriptional regulators; and
    c) transplanting the exposed cells into the individual.

3. A method for treating bone marrow cells from an individual having cancer prior to infusion of the bone marrow cells back into the individual, comprising the steps of:
    a) obtaining bone marrow cells from the individual; and
    b) exposing the bone marrow cells to a proliferation inhibiting amount of an antisense oligonucleotide having a sequence complementary to a sequence of RNA transcribed from a target gene present in the cells of the cancer, wherein said target gene is selected from the group consisting of genes that encode a molecule that regulates cell proliferation or viability.

4. A method for treating an individual having cancer comprising the steps of:
    a) obtaining bone marrow cells from the individual; and
    b) exposing the bone marrow cells to a proliferation inhibiting amount of an antisense oligonucleotide having a sequence complementary to a sequence of RNA transcribed from a target gene present in the cells of the cancer, wherein said target gene is selected from the group consisting of genes that encode a molecule that regulates cell proliferation or viability.
    c) transplanting the exposed cells into the individual.

5. A method for treating bone marrow cells from an individual having cancer prior to infusion of the bone marrow cells back into the individual, comprising the steps of:
    a) obtaining bone marrow cells from the individual; and
    b) exposing the bone marrow cells to a proliferation inhibiting amount of an antisense oligonucleotide having a sequence complementary to a sequence of RNA transcribed from a target gene present in the cells of the cancer, wherein said target gene is a gene that encodes a molecule that regulates cellular differentiation.

6. A method for treating an individual having cancer comprising the steps of:
    a) obtaining bone marrow cells from the individual; and
    b) exposing the bone marrow cells to a proliferation inhibiting amount of an antisense oligonucleotide having a sequence complementary to a sequence of RNA transcribed from a target gene present in the cells of the cancer, wherein said target gene is a gene that encodes a molecule that regulates cellular differentiation; and
    c) transplanting the exposed cells into the individual.

7. The method of claim 1, 2, 3, 4, 5 or 6 wherein said oligonucleotide has sufficient complementarity with the target gene to form a duplex having a melting temperature of at least about 40 degrees Centigrade under physiologic conditions.

8. The method of claim 2 or 4 or 6 comprising the additional step of administering to the individual a sufficient amount of a preparation containing oligonucleotides complementary to RNA transcribed from a target gene present in the cells of the cancer to kill the cancerous cells of the individual.

9. The method of claim 1, 2, 3, 4, 5 or 6 where the cancer is further defined as a cancer of cells of the hemopoietic system.

10. The method of claim 1, 2, 3, 4, 5 or 6 where the cancer is leukemia.

11. The method of claim 1, 2, 3, 4, 5 or 6 where the cancer is myeloid leukemia.

12. The method of claim 1, 2, 3, 4, 5 or 6 where the cancer is lymphoma.

13. The method of claim 1, 2, 3, 4, 5 or 6 where the cancer is breast cancer.

14. The method of claim 1, 2, 3, 4, 5 or 6 where the cancer is multiple myeloma.

15. The method of claim 1, 2, 3, 4, 5 or 6 where the cancer is gastrointestinal cancer.

16. The method of claim 1, 2, 3, 4, 5 or 6 where the target is a traitor gene.

17. The method of claim 1, 2, 3, 4, 5 or 6 wherein the oligonucleotide has a charged backbone.

18. The method of claim 1, 2, 3, 4, 5 or 6 wherein the oligonucleotide has an uncharged backbone.

19. The method of claim 1, 2, 3, 4, 5 or 6 where the oligonucleotide is a methylphosphonate oligonucleotide.

20. The method of claim 1, 2, 3, 4, 5 or 6 where the oligonucleotide is a phosphorothioate oligonucleotide.

21. The method of claim 1, 2, 3, 4, 5 or 6 where the oligonucleotide comprises at least 8 bases and is complementary to a sequence of RNA located 5' to the initiation condon of said target.

22. The method of claim 1, 2, 3, 4, 5 or 6 where the oligonucleotide comprises the sequence 3'-GGTCTGACGGAAGGCCCAGTGACGGTAC-5'.

23. The method of claim 1, 2, 3, 4, 5 or 6 where the oligonucleotide comprises at least 8 bases and is located within 40 bases of the initiation codon.

24. The method of claim 1, 2, 3, 4, 5 or 6 where the proliferation-inhibiting amount is 10-200 micromolar.

25. The method of claim 1, 2, 3, 4, 5 or 6 where the exposing step comprises:
   a) fractionating the bone marrow cells to obtain a mononuclear cell fraction, and
   b) culturing the mononuclear fraction together with a proliferation inhibiting amount of the oligonucleotide for at least about 1-10 days.

26. A method for treating bone marrow cells from an individual having cancer prior to infusion of the bone marrow cells back into the individual, comprising the steps of:
   a) obtaining bone marrow cells from the individual;
   b) exposing the bone marrow cells to a proliferation inhibiting amount of an antisense oligonucleotide having a sequence complementary to a sequence of RNA transcribed from a target gene present in the cells of the cancer, wherein said target gene is p53.

* * * * *

UNITED STATES PATENT AND TRADEMARK OFFICE
CERTIFICATE OF CORRECTION

PATENT NO. : 5,087,617
DATED : Feb. 11, 1992
INVENTOR(S) : Larry J. Smith

It is certified that error appears in the above-identified patent and that said Letters Patent is hereby corrected as shown below:

Column 1, line 14, please replace "proliferationinhibiting" with
--proliferation-inhibiting--.

Column 2, line 14, please delete the word "heterogenity" and insert the word --heterogeneity--.

Column 4, line 37, delete the word "suitable".

UNITED STATES PATENT AND TRADEMARK OFFICE
CERTIFICATE OF CORRECTION

PATENT NO. : 5,087,617
DATED : Feb. 11, 1992
INVENTOR(S) : Larry J. Smith

It is certified that error appears in the above-identified patent and that said Letters Patent is hereby corrected as shown below:

Column 4, line 37, after the word "targets" insert the words --are suitable--.

Column 4, line 48, after the word "selected" delete the comma.

Column 4, line 43, after the word "by" delete the comma.

Column 4, line 49, after the word "kill" add a comma.

UNITED STATES PATENT AND TRADEMARK OFFICE
CERTIFICATE OF CORRECTION

PATENT NO. : 5,087,617

DATED : Feb. 11, 1992

INVENTOR(S) : Larry J. Smith

It is certified that error appears in the above-identified patent and that said Letters Patent is hereby corrected as shown below:

Column 4, line 57, after the word "cancer" delete the comma.

Column 4, line 66, before the word "gastrointestinal" add the word --and--.

Column 5, line 1, after the word "backbones" delete the comma.

Column 5, line 3, after the word "oligonucleotides" delete the comma.

UNITED STATES PATENT AND TRADEMARK OFFICE
CERTIFICATE OF CORRECTION

PATENT NO. : 5,087,617
DATED : Feb. 11, 1992
INVENTOR(S) : Larry J. Smith

It is certified that error appears in the above-identified patent and that said Letters Patent is hereby corrected as shown below:

Column 8, line 59, delete the word "Kicke" and replace with --Dicke--.

Column 15, line 28, after the word "resuspended" delete the word "of".

Column 15, line 36, after "(200 mmole/1)" delete the comma.

Column 16, line 11, after the word "example" add a comma.

UNITED STATES PATENT AND TRADEMARK OFFICE
CERTIFICATE OF CORRECTION

PATENT NO. : 5,087,617
DATED : Feb. 11, 1992
INVENTOR(S) : Larry J. Smith

It is certified that error appears in the above-identified patent and that said Letters Patent is hereby corrected as shown below:

Column 16, line 18, after the word "morrow" add the word --and--.

Column 16, line 51, after "(1987)" delete the semicolon.

Column 16, line 52, delete the word "Chimeic" and replace with the word --chimeic--.

UNITED STATES PATENT AND TRADEMARK OFFICE
CERTIFICATE OF CORRECTION

PATENT NO. : 5,087,617
DATED : Feb. 11, 1992
INVENTOR(S) : Larry J. Smith

It is certified that error appears in the above-identified patent and that said Letters Patent is hereby corrected as shown below:

Column 20, claim 21, delete the word "condon" and replace with the word --codon--.

Signed and Sealed this

Twelfth Day of April, 1994

Attest:

BRUCE LEHMAN

Attesting Officer

Commissioner of Patents and Trademarks